United States Patent [19]
Lewis

[11] 3,943,918
[45] Mar. 16, 1976

[54] DISPOSABLE PHYSIOLOGICAL TELEMETRIC DEVICE

[75] Inventor: Ronald A. Lewis, Buffalo Grove, Ill.

[73] Assignee: Tel-Pac, Inc., Rochester, Minn.

[22] Filed: Dec. 2, 1971

[21] Appl. No.: 204,063

[52] U.S. Cl. ........ 128/2.1 A; 128/2.06 E; 200/61.19
[51] Int. Cl.² .......................................... A61B 5/04
[58] Field of Search...... 128/2.06 B, 2.06 E, 2.06 R, 128/2.1 A, 2.1 E, 2.1 R, 2.05 P, 2 P, 404, 417, 418; 200/61.08, 61.19

[56] References Cited
UNITED STATES PATENTS

| | | | |
|---|---|---|---|
| 3,212,496 | 10/1965 | Preston | 128/2.06 R |
| 3,253,588 | 5/1966 | Vuilleumier et al. | 128/2.1 A |
| 3,369,104 | 2/1968 | Lovercheck | 200/61.19 |
| 3,387,608 | 6/1968 | Figar | 128/2.06 E |
| 3,606,881 | 9/1971 | Woodson | 128/2.06 E |

*Primary Examiner*—William E. Kamm
*Attorney, Agent, or Firm*—Wegner, Stellman, McCord, Wiles & Wood

[57] ABSTRACT

A throwaway, one-time use signal sensing and telemetric transmitting device for use such as in the care of medical patients requiring a monitoring of a physiological function such as the cardiac function of the patient. The device includes one-time use self-powering battery means, adhesive means for attachment of the device to the patient and electrodes for sensing the physiological functioning. A disposable cover is removed to expose the adhesive means and the battery means are actuated to power the device at the time of use. The radio frequency transmitted signal is received on a suitable radio telemetry receiver for monitoring and recording as desired.

19 Claims, 6 Drawing Figures

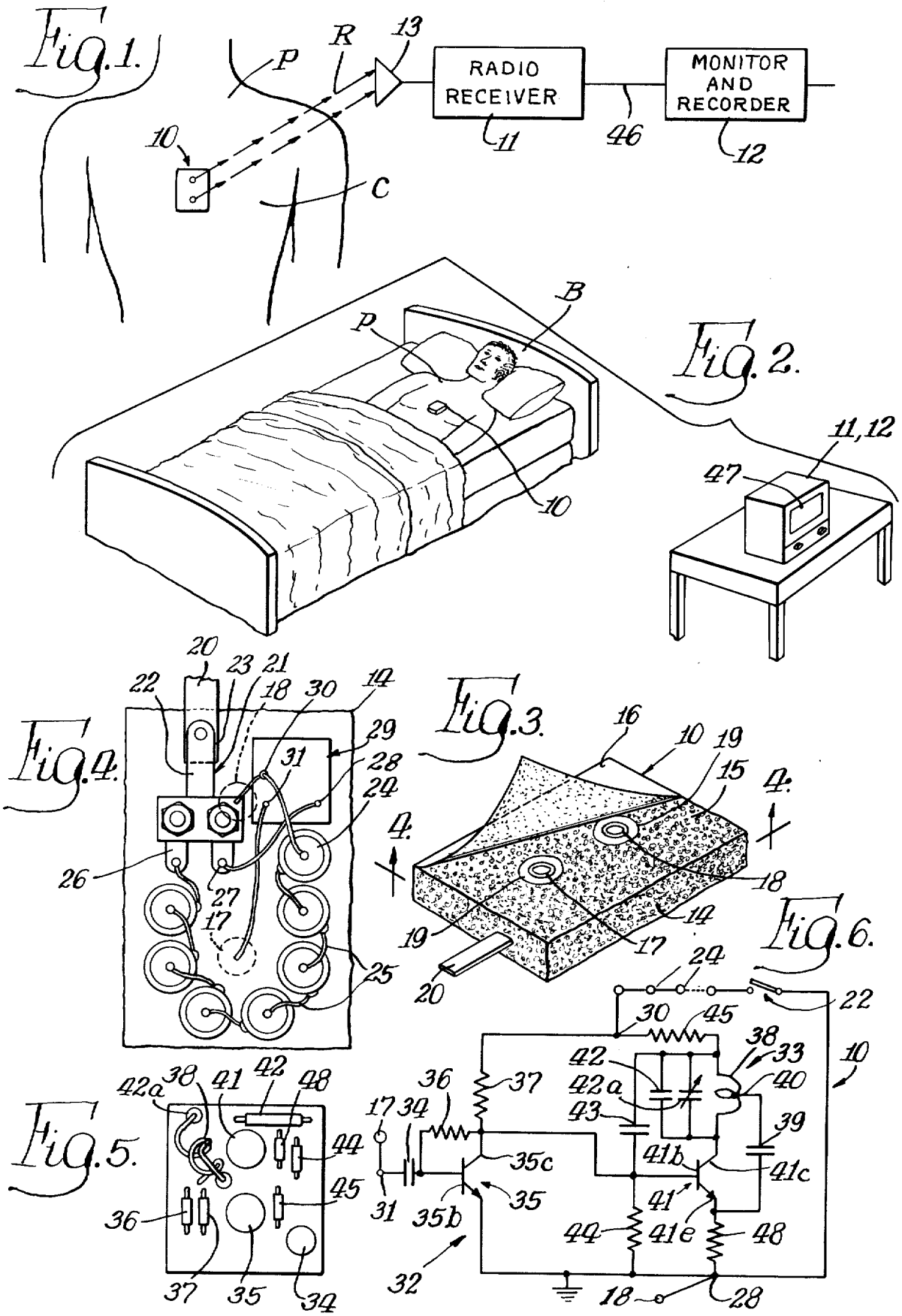

DISPOSABLE PHYSIOLOGICAL TELEMETRIC DEVICE

BACKGROUND OF THE INVENTION

1. Field of the Invention

This invention relates to physiological monitoring and recording devices, and in particular to telemetric forms of such devices.

2. Description of the Prior Art

Conventionally, the monitoring of a patient such as in an intensive care unit of a hospital has required vigilant surveillance by one or more nurses. More recently, monitoring means have been utilized in the form of electrical monitoring and recording devices which are connected to the patient by suitable electrical wires. Such conventional devices have required that the patient's bed be made electrically shockproof and it has been found that to suitably shockproof such a hospital bed costs approximately $2,500.00. Notwithstanding such expensive shockproofing, a number of patients have died each year as a result of electric shock because of failure of the system.

The use of such wiring limits the mobility of the patient and conventionally has required that the patient remain in the shockproof bed.

Because of the high cost of the equipment and the installation, the use thereof has been primarily limited to intensive care units of hospitals and, thus, such monitoring has not been readily available in connection with less serious patient problems.

It has been known in the prior art to use telemetric devices in connection with physiologic monitoring. One such device is shown in the Preston U.S. letters Pat. No. 3,212,496 which discloses a molecular physiological monitoring system wherein the voltage produced by the heart in the functioning thereof in sensed and transmitted to an EKG receiver and recording or display device. In Preston, the transducer system is implanted subcutaneously or externally.

Other patents which show different forms of transducers and telemetric physiological devices are shown in the U.S. letters Patent

| | | |
|---|---|---|
| 2,958,781 | Marchal et al | Radio-Physiological Method and Means |
| 3,144,017 | Muth | Pill-Type Swallowable Transmitter |
| 3,190,285 | Muth | Construction of a Battery Electrode for an Endo-Radiosonde |
| 3,343,528 | Kirkham | Electrocardiographic Switching System |
| 3,555,529 | Brown et al | Apparatus for Measuring Electric Field Radiation from Living Bodies |
| 3,572,316 | Vogelman et al | Physiological Signal Monitoring System |
| 3,583,392 | Frieberger | Method of Recording Recurring Events |

SUMMARY OF THE INVENTION

The present invention comprehends an improved throwaway, one-time use physiological signal sensing and transmitting telemetric device defined by a mounting element, electrodes carried by the mounting element, adhesive means carried by the mounting element for causing adherence of the mounting element to the skin of a patient with the electrodes in electrical-signal-receiving contact with the patient, a wireless transmitter carried by the mounting element connected to the electrodes for transmitting a signal corresponding to physiological information picked up by the electrodes, power means carried by the mounting element for operating the device, and means carried by the device for maintaining the device inoperative prior to a desired use and arranged to be readily manipulated to cause the device to be placed in a one-time operative condition, the element of the device being miniaturized to provide a low cost construction suitable economically to permit disposal of the device upon completion of a one-time use thereof.

The adhesive means of the device may comprise a nonallergenic adhesive backed pad carrying the sensing means and transmitting means. The electrodes may be maintained in electrical contact with the user's skin by the adhesive backed pad.

A battery may be provided in the device and means may be provided for preventing actuation of the battery until the desired use of the device.

The entire device may be made extremely small and at low cost permitting it to be economically considered as disposable after a one-time use. The electronics of the device may be formed as an integrated circuit chipboard or a discrete component printed circuit and the power requirements of the device may be made extremely small so that small, lightweight, low cost batteries may be employed in the device.

The adhesive pad may include suitable jelly for providing positive electrical contact of the electrodes with the user's body and may be provided with a removable protective cover maintaining the adhesive surface and jelly suitable for use upon removal of the cover.

BRIEF DESCRIPTION OF THE DRAWING

Other features and advantages of the invention will be apparent from the following description taken in connection with the accompanying drawing wherein:

FIG. 1 is a schematic representation of a patient provided with a signal sensing and telemetric transmitting device embodying the invention in connection with the transmitting of physiologic signals to a suitable receiver, monitor, and recorder;

FIG. 2 is a perspective view of the device in use in transmitting such signals;

FIG. 3 is a perspective view of the device with the protective cover partially removed;

FIG. 4 is a horizontal section taken substantially along the line 4—4 of FIG. 3;

FIG. 5 is an elevation of the electronic components of the device; and

FIG. 6 is a schematic wiring diagram of the electronic circuitry thereof.

DESCRIPTION OF THE PREFERRED EMBODIMENT

In the exemplary embodiment of the invention as disclosed in the drawing, a physiologic signal sensing and transmitting telemetric device generally designated 10 is shown to comprise a device adapted to be affixed to the chest C of a patient for sensing a physiological function of the patient such as the cardiac function and transmitting suitable radio signals R corresponding thereto to a receiver 11 and a suitable monitor and recording device 12. The receiver 11 may be provided with a suitable antenna 13 for receiving the radio signals R at a location remote from the patient. The receiver may be installed in the same room with the patient, or at a central surveillance area as desired within the range of the transmitting device 10. The patient may utilize a conventional hospital bed B which need not be electrically shockproofed and is free to move about within the range of the transmitter with the device 10 remaining attached to the patient's body in the manner of a small adhesive bandage which may preferably be of the nonallergenic type.

As shown in FIG. 3, device 10 may comprise a block 14 of suitable nonallergenic foam plastic having a nonallergenic adhesive coated front surface 15 normally covered by a suitable protective sheet 16. Nonallergenic electrodes 17 and 18 project outwardly from the surface 15 and a body of suitable electrically conductive nonallergenic jelly of conventional form 18 is provided in association with each electrode also suitably covered by the sheet 16 prior to use of the device. Each electrode illustratively may be formed of silver-silver chloride and comprise a circular electrode of approximately ¾ inch diameter with the electrodes being spaced apart approximately 1 inch on center from the block 14.

A manually operable element 20 may be provided for effecting connection of the battery device to the electrical circuitry thereof as will be brought out more fully hereinafter. Thus, the device may be stored in a sterile pack for extended periods of time within the normal shelf life of the batteries and made available substantially instantaneously for use by the simple removal from the sterile pack and removal of the protective cover sheet 16 and manipulation of the battery actuator 20.

As shown in FIG. 4, the device may comprise a suitable electrical switch means having a pair of blades 22, or contact and blade on the printed circuit board, biased to contact each other upon removal of the manual control element 20 which comprises an insulating strip having an inner end 23 normally disposed between the contact blades 22 and thereby maintaining the circuit from the battery open. Upon removal of the strip, the blade contacts close to establish the electrical circuit from the batteries 24 which, in the illustrated form, comprise a series of 7 small Mallory Type MP-675 cells. The block 14 is relatively small and illustratively, may have a size of approximately 3 inch × 3 inch × ½ inch. The block is preferably formed of an insulating foam material, such as foam rubber, so that the batteries may be placed in electrical series by suitable mounting on the block with electrical leads 25 extending between the successive batteries, as shown in FIG. 4. One end of the series of batteries is connected to terminal 26 of the switch 21. The other terminal 27 of switch 21 is connected to one terminal 28 of the electronic circuit means 29 and the other end of the battery series is connected directly to the other terminal 30 of the device 29. The electrodes 17 and 18 are connected respectively to a third terminal 31 and the terminal 28 of device 29, as shown in FIG. 4.

The electronic device 29 may comprise an integrated circuit chipboard or a discrete component printed circuit having extremely small size and being extremely economical of manufacture. The device 29 comprises means for amplifying the signal sent by the electrodes and transmitting it as a frequency modulated radio signal to the receiver 11. Broadly, the device 10 includes an amplifier portion 32 and a transmitter portion 33. The transmitter preferably operates at a transmitting frequency of 204 megacycles where the 7 batteries 24 provide a 9-volt output. The frequency of the transmitter is variable between 200 megacycles to 215 megacycles by suitable variation in the battery voltage and changing of the Q of the tank circuit of the Hartley oscillator transmitter 33. The transmitter draws approximately 3 milliamps at approximately 9 volts, so that the batteries as disclosed are continuously operable for a period of at least one week. The operating range of the transmitter is up to approximately 100 feet or more.

Referring to FIG. 6, electrode 18 is connected to terminal 28 and electrode 17 is connected to terminal 31 to provide an input to the amplifier stage 32 of the device 10. Terminal 31 is connected through a 47 microfarad condenser to a base 35b of NPN transistor 35, or FET having the same characteristics. Base bias is provided by a 220 kilohm resistor 36 coupled from the collector 35c and base 35b of NPN transistor 35. An output is taken from the junction between a 15 kilohm load resistor 37 and collector 35c of NPN transistor 35. The oscillator 33 comprises a modified Hartley oscillator device utilizing a tank circuit of a coil 38 illustratively having 2 flat hairpin turns ¼ inch long by ⅛ inch between, printed on the foil side of the board, or 2 flat hairpin turns ¼ inch long by ⅛ inch between, of No. 22 solid wire mounted in line on the component side of the board. A suitable capacitor 39 is connected between center tap 40 of the coil and the emitter 41e of an osciallator transistor 41. The tank circuit further includes a 22 picofarad capacitor 42. A 2–9 picofarad trimmer capacitor 42a is connected across capacitor 42 for fine tuning. The amplified signal from amplifier 32 is delivered to base 41b of transistor 41 for modulating a radio frequency output of the transmitter. The base is further coupled to a junction between capacitor 43 and a resistor 44 which are serially connected from emitter 41e to a junction between a load resistor 45 and coil 38.

The effective input impedance of the amplifier is approximately 10 kilohms and provides a stage gain of approximately 13 with a frequency response of from approximately 0.015 to 100 c.p.s. The input power to the oscillator is approximately 1 milliwatt. In the illustrated embodiment, the transistors 35 and 41 comprise Fairchild 2N708 or FET 2N5485 transistors having the same characteristics.

In operation, the cardiac function signal applied to electrodes 17 and 18 upon amplification by the amplifier portion 32 of the device is transmitted from the coil 38 which serves as an FM radio transmitter with the intelligence being modulated thereon in the Hartley oscillator transmitter portion 33 of the device. This signal is received by the radio receiver 11 through the antenna 13 connected thereto and may be utilized as desired such as by delivery to a suitable monitor, alarm and recorder device 12. The monitor and recorder device may be physically associated with the radio receiver or may be remotely associated and connected thereto by suitable wires 46 as desired. In the illustrated embodiment, the receiver comprises a Fisher 500 FM receiver provided with a Hewlett-Packard 350–2700 preamplifier. The preamplifier may be provided with a high and low filter for filtering out high frequency interference.

Thus, in illustrating the invention, the device 10 has been shown as a built-up amplifier and transmitter utilizing conventional transistors and circuit components. Illustratively, the device 10 may be laid out as shown in FIG. 5. As discussed above, however, the circuit is amenable to provision in the form of an integrated circuit chipboard or a discrete component printed circuit for effectively minimized cost and size.

Thus, the device may be applied quickly to a patient by the simple readying thereof by removing the sheet 16 and adhesive attachment to the patient's chest along the sternum with the pullout strip 20 at the top. The receiver 11 is tuned to the output frequency of the transmitter 33, which illustratively may be 204 megacycles. Switch 21 is then closed by removing the strip 20 from between the blades 22 whereupon the FM carrier will replace the institutional noise picked up by the transmitter as a quiet hush. The electrical functioning of the heart will then be viewable on the oscilloscope 47 of the receiver-recorder 11, 12. The device 10 is applied in the manner of a conventional bandage to the patient's body without complicated or extensive preparation of the patient. As the device is extremely simple and economical of construction, it may be utilized as a one-time use, throwaway device which permits high mobility of the patient while yet providing continuous monitoring of the sensed physiological function.

The foregoing disclosure of specific embodiments is illustrative of the broad inventive concepts comprehended by the invention.

I claim:

1. A throwaway, one-time use physiological signal sensing and telemetric transmitting device comprising: a mounting element; electrodes carried by said mounting element; adhesive means carried by said mounting element for causing a substantially one-time adherence of the mounting element to the skin of a patent with the electrodes in electrical-signal-receiving contact with said patient; a wireless transmitter carried by said mounting element connected to said electrodes for transmitting a signal corresponding to physiological information picked up by said electrodes; battery means carried by said mounting element for self-powered operating of said device; and means carried by the device for maintaining the device inoperative prior to a desired use and irreversibly manually operable to cause the transmitter to be placed in a one-time energized operative condition, the elements of the device being miniaturized to provide a low cost construction suitable economically to permit disposal of the device upon completion of a one-time use thereof.

2. The throwaway sensing and transmitting device of claim 1 having means for covering the electrodes prior to use of the device.

3. The throwaway sensing and transmitting device of claim 1 wherein said electrodes are laterally surrounded by said adhesive means.

4. The throwaway sensing and transmitting device of claim 3 having means for covering the adhesive means and the electrodes prior to use of the device.

5. The throwaway sensing and transmitting device of claim 1 wherein said mounting element comprises a body of foamed plastic.

6. The throwaway sensing and transmitting device of claim 5 wherein said transmitter is enclosed in said mounting element.

7. The throwaway sensing and transmitting device of claim 5 wherein said battery means is enclosed in said mounting element.

8. The throwaway sensing and transmitting device of claim 1 wherein said means for maintaining the device inoperative includes a switch for controlling delivery of power from said battery means to said transmitting means and means for effectively irreversibly closing said switch to maintain the transmitter engaged for the useful life of the device.

9. The throwaway sensing and transmitting device of claim 8 wherein said switch includes a pair of contacts biased toward a contacting relationship and said means for maintaining the device inoperative includes an insulator removably disposed between said contacts and means for effecting irreversible withdrawing of the insulator to permit said contacts to have maintained engagement and thereby energize the device continuously.

10. The throwaway sensing and transmitting device of claim 1 wherein means are provided for providing good electrical contact between the patient's skin and said electrodes.

11. The throwaway sensing and transmitting device of claim 1 wherein said mounting element comprises a nonallergenic pad.

12. The throwaway sensing and transmitting device of claim 1 wherein said mounting element is a nonallergenic material.

13. The throwaway sensing and transmitting device of claim 1 wherein said adhesive means is a nonallergenic material.

14. The throwaway sensing and transmitting device of claim 1 wherein said electrodes are nonallergenic material.

15. The throwaway sensing and transmitting device of claima 1 wherein nonallergenic means are provided for providing good electrical contact between the patient's skin and said electrodes.

16. A throwaway, one-time use physiological signal sensing and telemetric transmitting device comprising: means for sensing a physiological condition of a patient and providing an input signal in conformity therewith; means for transmitting a radio frequency signal modulated by said input signal for reception by a suitable receiver; an adhesive backed pad carrying said sensing means and said transmitting means for adherence to a patient's skin as a result solely of urging of the adhesive back of the pad thereagainst; and battery means permanently associated with said pad and electrically associated with said transmitting means, said transmitting means including switch means for irreversibly actuating the device from said battery means at the desired time of use while maintaining the device inoperative until such time.

17. The throwaway sensing and transmitting device of claim 16 wherein said sensing means comprises electrodes adapted to be maintained in electrical contact with the user's skin by said adhesive backed pad.

18. The throwaway sensing and transmitting device of claim 16 wherein said transmitting means includes means for amplifying the input signal.

19. The throwaway sensing and transmitting device of claim 16 wherein said adhesive backed pad is nonallergenic.

* * * * *